United States Patent [19]
Botich et al.

[11] Patent Number: 6,004,278
[45] Date of Patent: Dec. 21, 1999

[54] FLUID COLLECTION DEVICE WITH RETRACTABLE NEEDLE

[75] Inventors: Michael J. Botich, Oxnard; Thor R. Halseth, Simi Valley, both of Calif.

[73] Assignee: MDC Investment Holdings, Inc., Wilmington, Del.

[21] Appl. No.: 08/761,088

[22] Filed: Dec. 5, 1996

[51] Int. Cl.⁶ ........................................ A61B 5/00
[52] U.S. Cl. .................................. 600/576; 604/198
[58] Field of Search ............................. 600/576, 577, 600/583; 604/110, 195, 198

[56] References Cited

U.S. PATENT DOCUMENTS

| | | |
|---|---|---|
| 3,123,073 | 3/1964 | Barr, Sr. et al. . |
| 3,159,159 | 12/1964 | Cohen . |
| 3,469,572 | 9/1969 | Nehring . |
| 3,874,367 | 4/1975 | Ayres . |
| 4,150,666 | 4/1979 | Brush . |
| 4,307,731 | 12/1981 | Kaufman ................. 128/766 |
| 4,418,703 | 12/1983 | Hoch et al. .............. 128/766 |
| 4,507,117 | 3/1985 | Vining et al. ............ 604/196 |
| 4,642,103 | 2/1987 | Gettig .................... 604/234 |
| 4,710,170 | 12/1987 | Haber et al. ............ 604/110 |
| 4,710,173 | 12/1987 | McFarlane . |
| 4,758,231 | 7/1988 | Haber et al. ............ 604/198 |
| 4,774,964 | 10/1988 | Bonaldo .................. 128/763 |
| 4,790,827 | 12/1988 | Haber et al. ............ 604/198 |
| 4,795,445 | 1/1989 | Jensen .................... 604/240 |
| 4,813,426 | 3/1989 | Haber et al. ............ 128/763 |
| 4,822,343 | 4/1989 | Beiser .................... 604/187 |
| 4,838,863 | 6/1989 | Allard et al. ........... 604/110 |
| 4,850,374 | 7/1989 | Diaz-Ramos ............ 128/763 |
| 4,871,355 | 10/1989 | Kikkawa ................. 604/198 |
| 4,892,107 | 1/1990 | Haber .................... 128/763 |
| 4,904,242 | 2/1990 | Kulli ..................... 604/110 |
| 4,915,702 | 4/1990 | Haber .................... 604/198 |
| 4,917,101 | 4/1990 | Horn ..................... 128/763 |
| 4,947,863 | 8/1990 | Haber et al. ............ 128/764 |
| 4,994,034 | 2/1991 | Botich et al. ........... 604/110 |
| 5,067,490 | 11/1991 | Haber .................... 128/763 |
| 5,070,885 | 12/1991 | Bonaldo ................. 128/763 |
| 5,086,780 | 2/1992 | Schmitt .................. 128/763 |
| 5,115,817 | 5/1992 | Sarstedt . |
| 5,125,414 | 6/1992 | Dysarz ................... 128/763 |
| 5,188,599 | 2/1993 | Botich et al. .......... 604/110 |
| 5,201,716 | 4/1993 | Richard ................. 604/187 |
| 5,219,333 | 6/1993 | Sagstetter et al. ...... 604/110 |
| 5,259,392 | 11/1993 | Schmitt ................. 128/763 |
| 5,407,431 | 4/1995 | Botich et al. .......... 604/110 |
| 5,423,758 | 6/1995 | Shaw .................... 604/110 |
| 5,518,004 | 5/1996 | Schraga ................. 128/763 |
| 5,531,694 | 7/1996 | Clemens et al. ........ 604/110 |
| 5,533,974 | 7/1996 | Gaba ..................... 604/110 |
| 5,578,015 | 11/1996 | Robb .................... 604/195 |

*Primary Examiner*—Max Hindenburg
*Attorney, Agent, or Firm*—Stephen H. Eland; Dann, Dorfman, Herrel and Skillman

[57] ABSTRACT

A needle retraction mechanism for a needle bearing medical device is provided. The needle retainer selectively retains the needle in a projecting configuration in which the sharpened tip of the needle projects outwardly from the device. The needle retaining mechanism has an axial projection configured to provide at least one finger, and preferably a plurality of separable fingers that are joined together to form a bore.

31 Claims, 7 Drawing Sheets

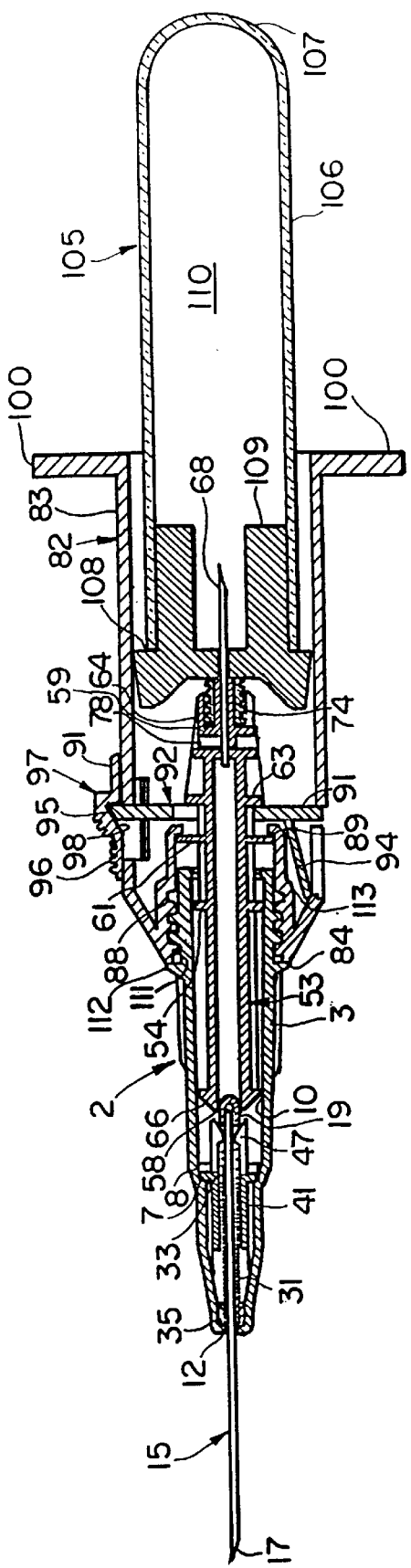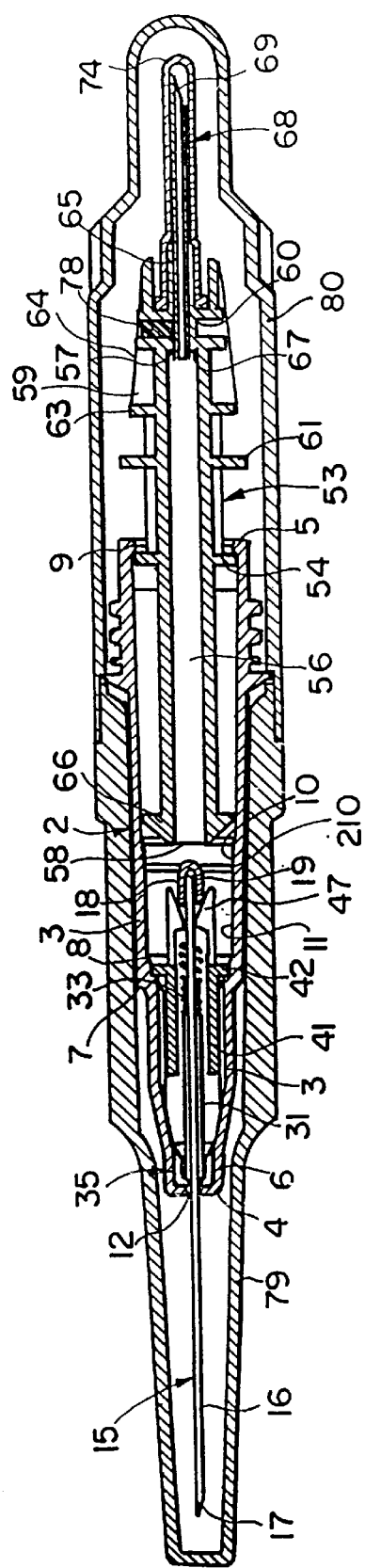
FIG. 1
FIG. 2

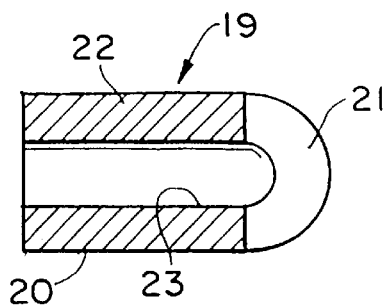
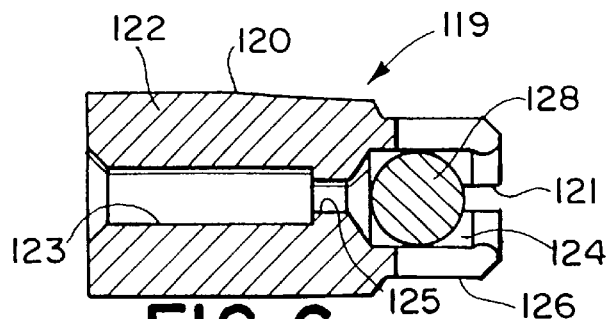
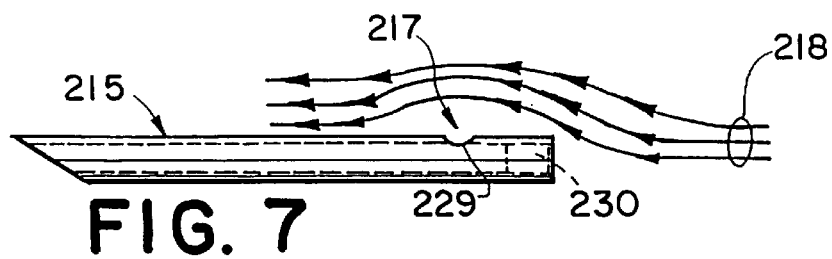
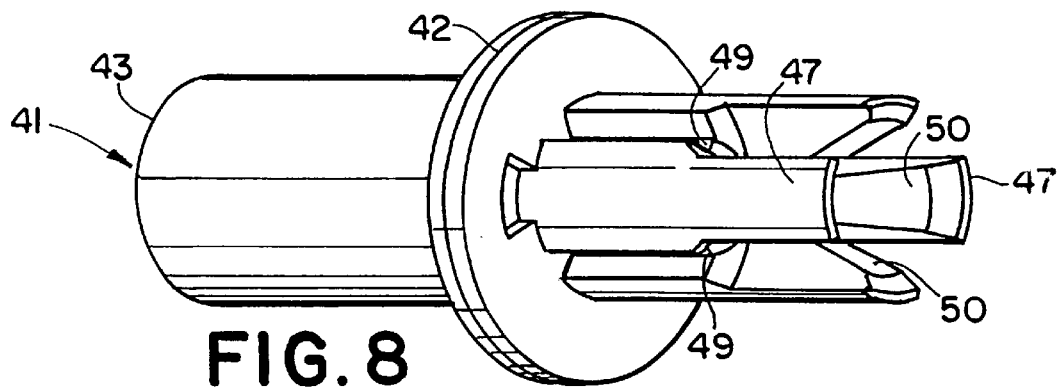
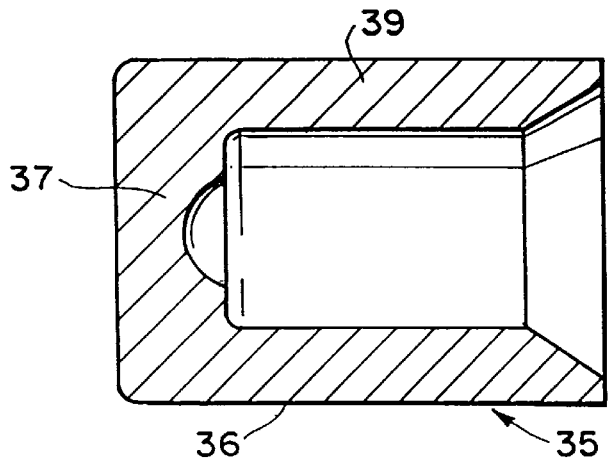

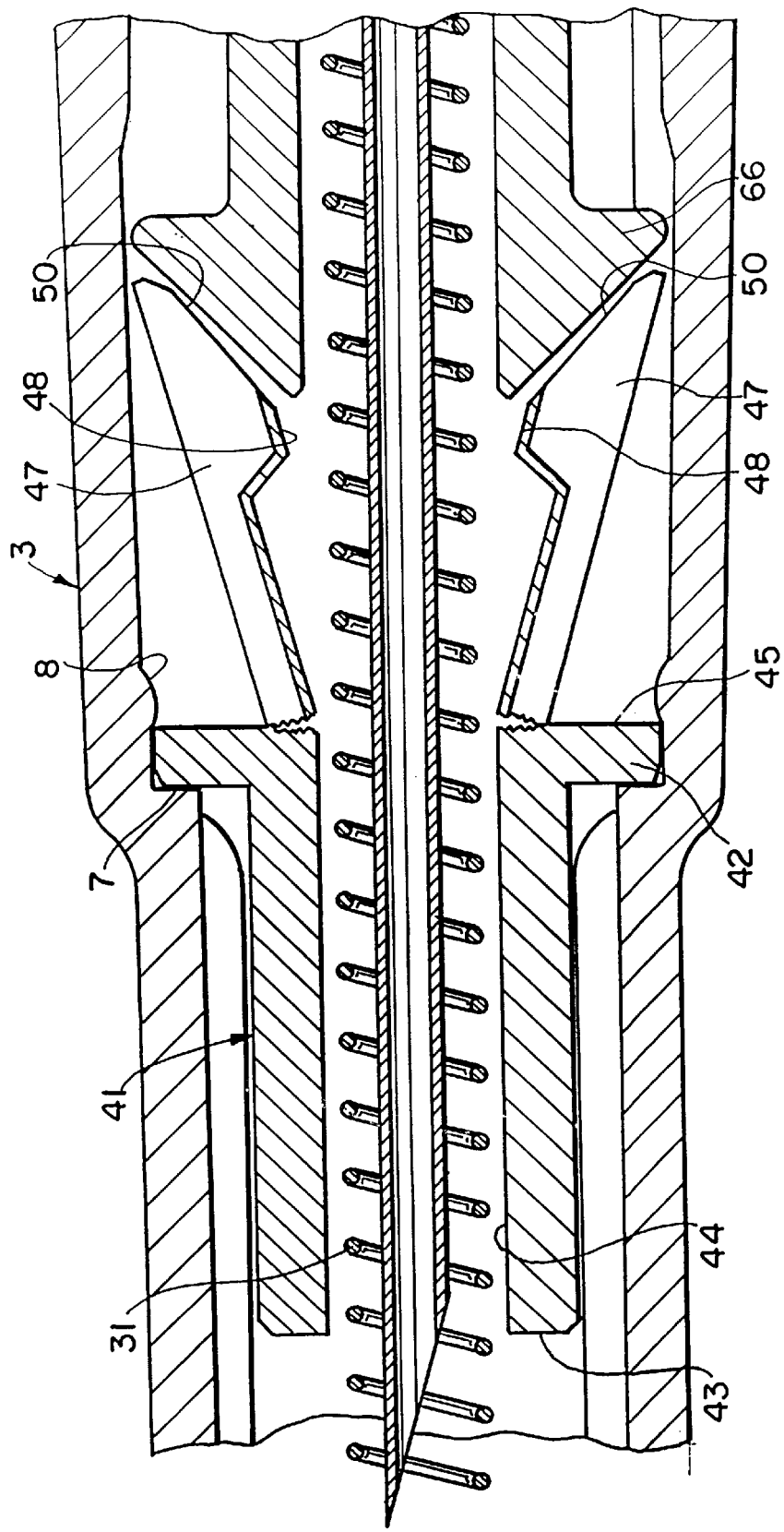

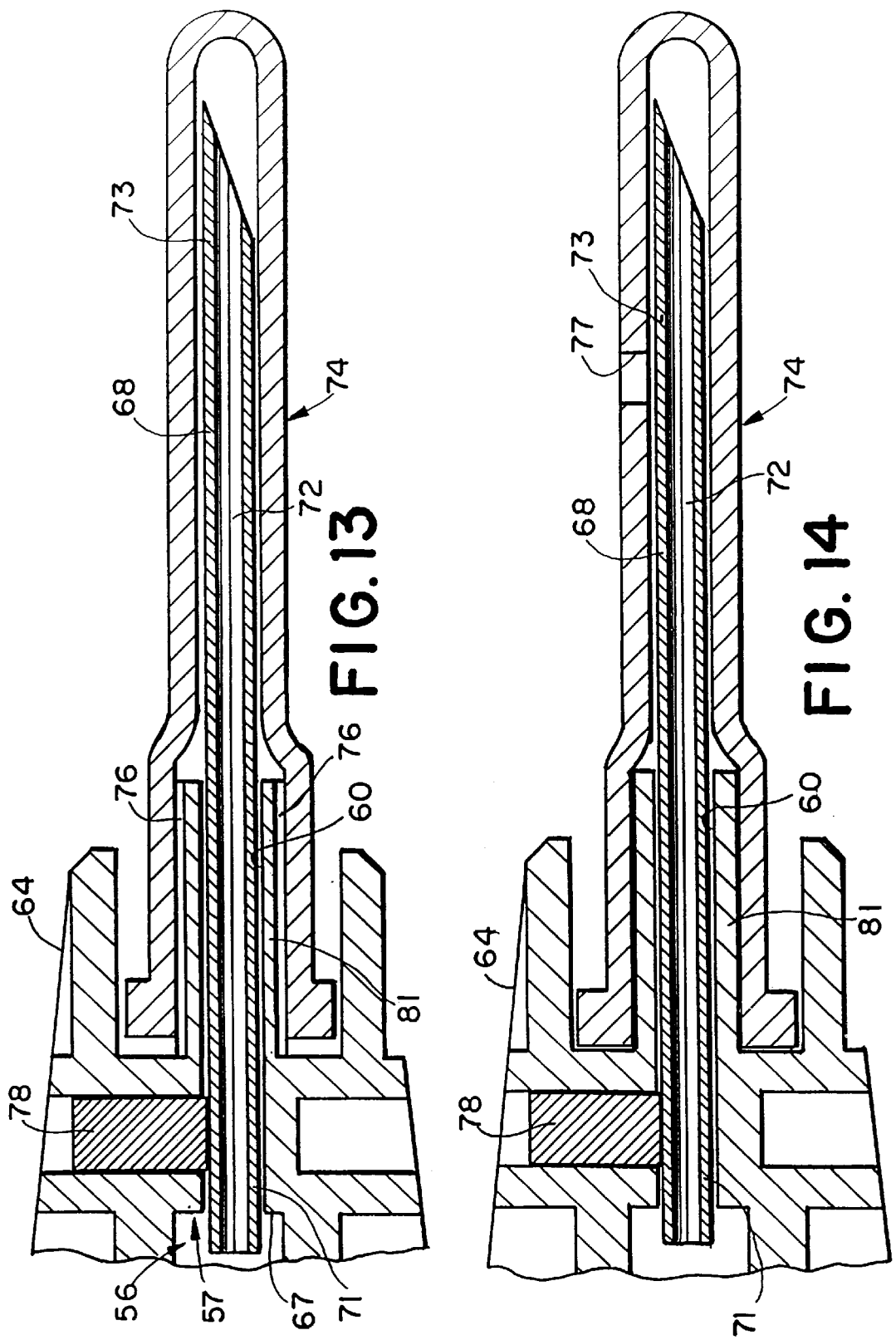

FLUID COLLECTION DEVICE WITH RETRACTABLE NEEDLE

FIELD OF THE INVENTION

The present invention relates to fluid collection devices for sampling fluid from a patient. More specifically, the invention relates to such a device having a retractable needle feature for rendering the device non-reusable and safely disposable.

BACKGROUND OF THE INVENTION

Various types of medical devices employ a needle for piercing the skin of a patient for diagnostic or therapeutic purposes. One such device is a blood collection device which includes a needle for piercing a blood vessel of the patient to allow blood to be sampled from the patient. When the needle is inserted into the blood vessel of the patient, blood is withdrawn through the needle into a vacuum collection tube. Handling of such needle-bearing medical devices after the needle is withdrawn from the patient can result in transmission of various pathogens, most notably human immune virus (HIV), to uninfected medical personnel, due to an inadvertent prick.

Since the mid-1980s, concern over the risk of accidental needle stick injuries has spawned a number of design approaches for safety needle devices. Such devices can be broadly categorized as sliding sheath needle devices, wherein a physical barrier is positioned about the needle tip after use, and needle-retraction devices, wherein the tip of the needle is withdrawn into the device after use. The category of needle retraction devices can be further subdivided into manual and automatic retraction devices. Manual retraction devices, as exemplified by U.S. Pat. No. 4,026,287 to Haller, U.S. Pat. No. 4,592,744 to Jagger, U.S. Pat. No. 4,808,169 to Haber et al. and U.S. Pat. No. 5,067,490 to Haber, require the user to pull or slide a needle-engaging mechanism rearwardly for a sufficient distance to withdraw the needle into the device. In automatic needle retraction devices, a biasing member, such as a spring, is employed to withdraw the needle into the device in response to activation of some release mechanism on the part of the user. Such devices are exemplified by U.S. Pat. No. 4,813,426 to Haber et al. and U.S. Pat. No. 5,125,414 to Dysarz.

U.S. Pat. No. 4,747,831 assigned to Becton Dickinson and U.S. Pat. No. 4,900,307 to Kulli show respective automatic retractable-needle catheter stylets and syringes. The devices shown in the last-mentioned two patents are disclosed to be actuatable on the part of the user by applying a simple unitary motion that entails a simple single-stage movement in just one direction. Specifically, these latter patents show devices in which retraction is effected by depressing a single surface or member for a short distance in a single direction. Hence, during preparation for use of such devices, the user must be mindful not to prematurely trigger the needle retraction mechanism by accidentally contacting the surface for actuating the retraction mechanism. Because medical needle bearing devices are often employed under distracting circumstances, it would be desirable to provide an automatic needle retraction-mechanism in which a compound action or dual motion is required by the user in order to effect automatic retraction of the needle. Such a mechanism would desirably require the user to act upon more than one surface of the retraction mechanism to effect withdrawal of the needle into the device. It further would be desirable to require that such actions occur along different directional axes to further decrease the likelihood of undesired or accidental premature retraction of the needle.

Of the aforementioned prior art devices which have automatic retraction, all require a needle structure having an enlarged head, lip or rim extending radially outwardly from the axis of the needle to provide a block or enlarged surface on the needle which is biased toward retraction by the spring and which can be restrained against retraction by a latching mechanism. In such devices, failure of the latch mechanism can occur to cause premature retraction of the needle. Hence, it would be desirable to provide an automatic needle retraction mechanism in which the latch mechanism operates more directly upon the needle, rather than through a block or rim surface on the needle.

After use of a needle bearing medical device, a small volume of contaminated fluid or blood may remain inside the needle after it is withdrawn from the patient. Depending upon the gauge of the needle used with the device, such residual fluid or blood may be ejected from the forward end of the needle during the rearward acceleration experienced in retraction of the needle. Such forward fluid ejection can result from insufficient capillary adhesion to retain the residual fluid against inertial forces, or against the hydraulic force exerted upon the residual fluid by inrushing fluid or air during rearward acceleration in retracting the needle. It would further be desirable to provide a structure in an automatic needle retraction device that would prevent such ejection of residual blood or fluid from the forward end of the needle during retraction.

SUMMARY OF THE INVENTION

In accordance with one aspect of the present invention, there is provided a needle retraction mechanism for a needle bearing medical device wherein a needle retaining member is bonded directly to the needle for selectively holding the needle in a projecting configuration from the device. The needle retaining member has an axial extension configured to provide a plurality of separable fingers that are joined about a central bore for holding the needle axially within the bore. Mutual engagement between the fingers and the needle can be enhanced by adhesive or thermal bonding. The needle retainer is positioned within the device to restrain the needle against rearward bias exerted upon the needle by a spring. The spring is preferably also bonded directly to the needle, so that neither the bias force or the counteracting restraining force is required to be mediated by any additional structure connected to the needle.

In accordance with another aspect of the present invention, the needle bearing medical device is provided with an automatic retraction mechanism in which the user is required to execute a dual or compound motion in order to actuate the needle for withdrawing the needle into the device by movement of a biasing member. The preferred compound motion requires the user to perform two motions on surfaces of the device and further these motions are designed to be in distinct directions in order to assure intentional needle retraction.

In accordance with another aspect of the present invention, there is provided a needle structure for use with an automatic retraction mechanism in a needle bearing device, wherein the needle structure includes means for preventing residual fluid from being ejected outwardly from the needle during rearward acceleration of needle retraction. The needle structure is configured to produce a partial vacuum within the rear of the needle during retraction by closure of a check valve mounted to the rear of the needle. In an alternative embodiment, a hole is formed in the sidewall of the needle near a closed rear end of the needle, so that the partial vacuum is provided by a zone of reduced pressure generated in the vicinity of the hole by fluid flow around the end of the needle during retraction.

BRIEF DESCRIPTION OF THE DRAWINGS

The foregoing summary, as well as the following detailed description of the preferred embodiments of the present invention, will be better understood when read in conjunction with the accompanying drawings, in which:

FIG. 1 is a sectional view of a retractable needle fluid collection device in accordance with the present invention;

FIG. 2 is an enlarged sectional view of the retractable needle assembly portion of the retractable needle fluid collection device of FIG. 1, showing the retractable needle assembly portion in an as-shipped configuration with front and rear protective caps positioned thereon;

FIG. 5 is a sectional view of a check valve member positioned over the rear end of the retractable needle of the device of FIG. 1;

FIG. 6 is a sectional view of an alternative check valve for being positioned over the rear end of the retractable needle of the device of FIG. 1;

FIG. 7 is a perspective view of an alternative needle design for use in the fluid collection device of FIG. 1, and illustrating lines of fluid flow about the needle during retraction;

FIG. 8 is a side elevational view of the needle retainer structure for selectively holding the needle of the fluid collection device of FIG. 1;

FIG. 10 is an enlarged fragmentary sectional view of the needle retainer of the fluid collection device of FIG. 1, showing the condition of the needle retainer, needle and biasing spring after retraction;

FIG. 11 is an enlarged sectional view of the sealing member for the end of the housing through which the retractable needle extends;

FIG. 13 is an enlarged fragmentary sectional view of the rear portion of the needle carrier assembly of FIG. 1 showing the fixed needle for puncturing the fluid collection tube; and FIG. 14 is an enlarged sectional view of an alternative configuration for the rear portion of the needle carrier assembly of FIG. 1.

DETAILED DESCRIPTION OF THE PREFERRED EMBODIMENTS

Figure 3:
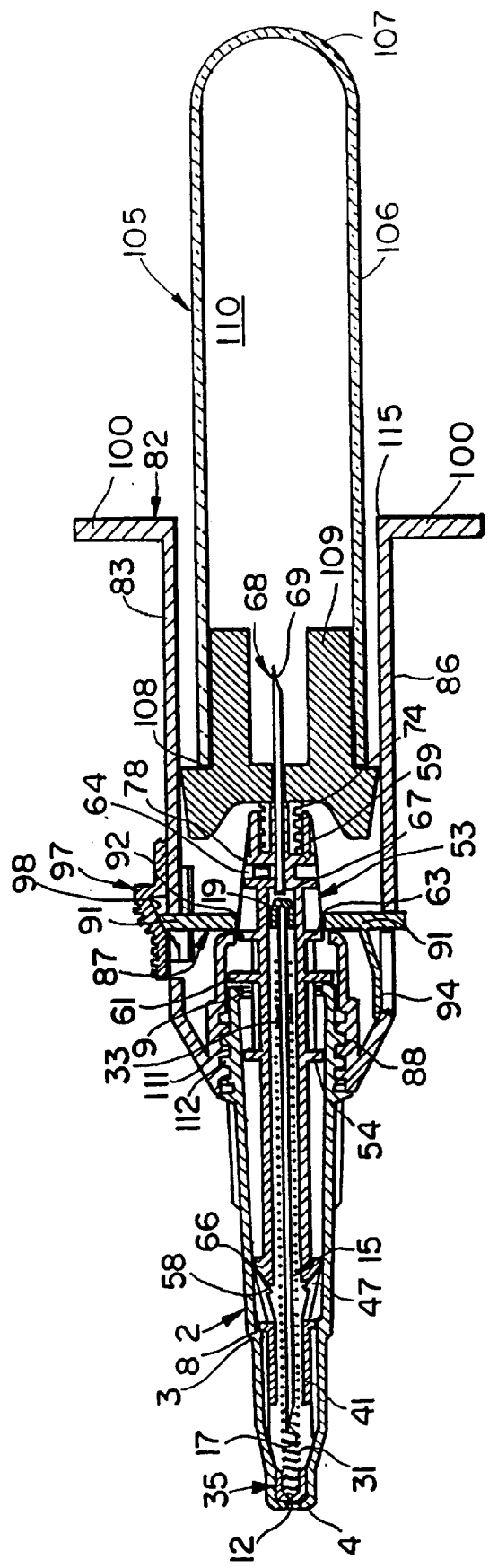
FIG. 3 is a sectional view of the retractable needle fluid collection device of FIG. 1, showing the needle in its retracted position.

Referring to FIG. 1, there is shown a fluid collection device in accordance with the present invention. The device comprises a needle carrier structure generally designated 2 for retaining a forwardly projecting needle 15 and a rearwardly projecting needle 68. A re-usable holder adapter generally designated 82 is mounted to the rear of the needle carrier structure for receiving a vacuum collection tube generally designated 105. After use of the device, the holder adapter 82 may be removed, and the needle carrier structure discarded.

The needle carrier structure 2 is shown in an as-shipped condition or configuration in FIG. 2. The needle carrier 2 comprises a barrel 3 having a partially closed forward end 4 and an open rear end 5. A needle 15 is positioned for use at the forward end 4 of the barrel 3 of the needle carrier 2. The needle 15 comprises a sharp forward end or tip 17 suitable for use in fluid sampling, such as for blood sampling by accessing a patient's vein. The needle 15 is preferably made of a biologically compatible material which can be easily sterilized, such as stainless steel. The forward portion of the needle 15 extends through an opening or axial hole 12 in the forward end 4 of the barrel 3 of the needle carrier 2. The rear portion of the needle 15 extends generally axially into the barrel 3 of the needle carrier 2. A second or rear needle 68 projects rearwardly from the needle carrier 2 into the areas of the holder adapter 82 which receives the vacuum collection tube 105.

During shipment, storage, or other handling of the needle carrier structure 2 prior to use, the tip 17 of the needle 15 is preferably surrounded and shielded by a front cap or sheath 79 that is removably attached to the exterior of the needle carrier 2. Likewise, the rear portion 73 of the rear needle 68 is preferably surrounded and shielded by a rear cap or sheath 80 during shipment, storage or other handling of the needle carrier structure 2 prior to use.

The front and rear caps 79 and 80 are held upon the needle carrier 2 by, for example, cooperative frictional engagement between the surface protrusion of the exterior of the needle carrier 2 and annular mating recesses of the front and rear caps 79 and 80, as shown in FIG. 2.

A spring 31 surrounds a portion of the needle 15 within the forward end of the barrel 3. The spring is compressed therein and connected to the needle 15 for biasing the needle 15 toward the rear end 5 of the barrel 3. The spring 31 is preferably bonded to the needle 15 by an adhesive 33, such as an epoxy, preferably an ultraviolet (UV) curable adhesive, such as "LOCTITE 3001", which is distributed by Loctite Corp. The spring 31 may be bonded to the needle 15 at a location spaced from the rear end of the spring 31, so that one or more coils of the spring 31 can be grasped during the bonding process to insure that the spring 31 and needle 15 are properly oriented and bonded together.

Figure 12:
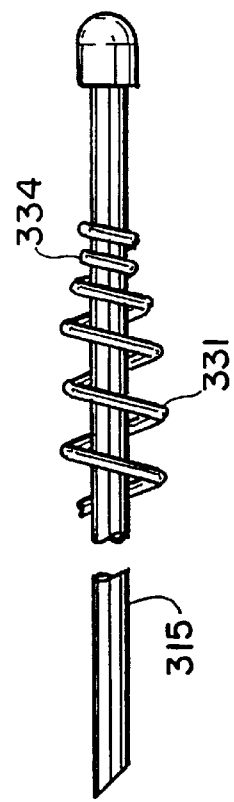
FIG. 12 is a side elevational view of an alternative arrangement for attaching the biasing spring to the retractable needle.

Alternatively, as shown in FIG. 12, wherein parts similar to those in FIG. 2 are shown by the same number designator with the addition of 300 thereto, the spring 331 may be attached to the needle 315 by crimping the spring 331 to the needle 315 to form a reduced diameter portion 334 for the spring 331. The spring 331 then exerts a rearward bias upon the needle 315 by virtue of a frictional engagement therebetween. In this arrangement, the reduced diameter portion 334 of the spring 331 may also be bonded to the needle 315 by adhesive to ensure permanent coupling of the spring to the needle.

Referring again to FIG. 1, a sealing member 35, such as a resilient cup, washer, silicone plug puncturable disc or the like, is positioned within the forward end 4 of the barrel 3 of the needle carrier 2. As best seen in FIG. 11, the preferred sealing member 35 comprises a resilient cup 36. A puncturable membrane 37 forms the forward end 38 of the sealing member 35. The membrane 37 is sufficiently thin to be pierced by the tip 17 of the needle 15 to allow the needle 15 to extend outwardly from the forward end 4 of the barrel 3 of the needle carrier 2. In this extended configuration for the needle from the needle carrier, the membrane 37 provides a fluid-tight seal about the interior of the axial hole 12 in the forward end 4 of the barrel 3. The membrane 37 is sufficiently resilient to seal the axial hole 12 after the needle 15 has been retracted, to prevent fluid from leaking out of the barrel 3 when the needle is retracted. The sealing member 35 also promotes axial alignment of the needle 15 and the spring 31 within the barrel 3, by holding the forward end 40 of the spring 31 within a tubular portion 39 of the resilient cup 36. Additionally, the sealing member 35 helps to protect the tip 17 of the needle 15 from being damaged by contact with the interior of the barrel 3 when the needle 15 is inserted into the barrel 3 during assembly.

Referring again to FIG. 2, a needle retainer 41 is positioned within a forward portion of the barrel 3 for selectively retaining the needle 15 in a configuration projecting outwardly from the needle carrier. A flange 42 is formed on the needle retainer 41 for engagement with a complementary groove 7 formed about the interior of the barrel 3 for orienting and fixing the needle retainer in position. An annular detent 8 is formed on the inner surface of the barrel 3 of the needle carrier 2 to prevent the needle retainer 41 from being dislodged from its position in the needle carrier 2. Holding of the needle retainer 41 in position in the interior of the barrel 3 may be further assured by epoxy or ultrasonic welding.

The forward end 43 of the needle retainer 41 is generally cylindrical. An axial bore 44 is formed in the needle retainer 41 for housing a portion of the needle 15 and the spring 31. The rear portion of the needle retainer 41 is provided with a latching structure or mechanism for selectively retaining the needle 15 in its projecting position from the needle carrier 2.

Figure 9:
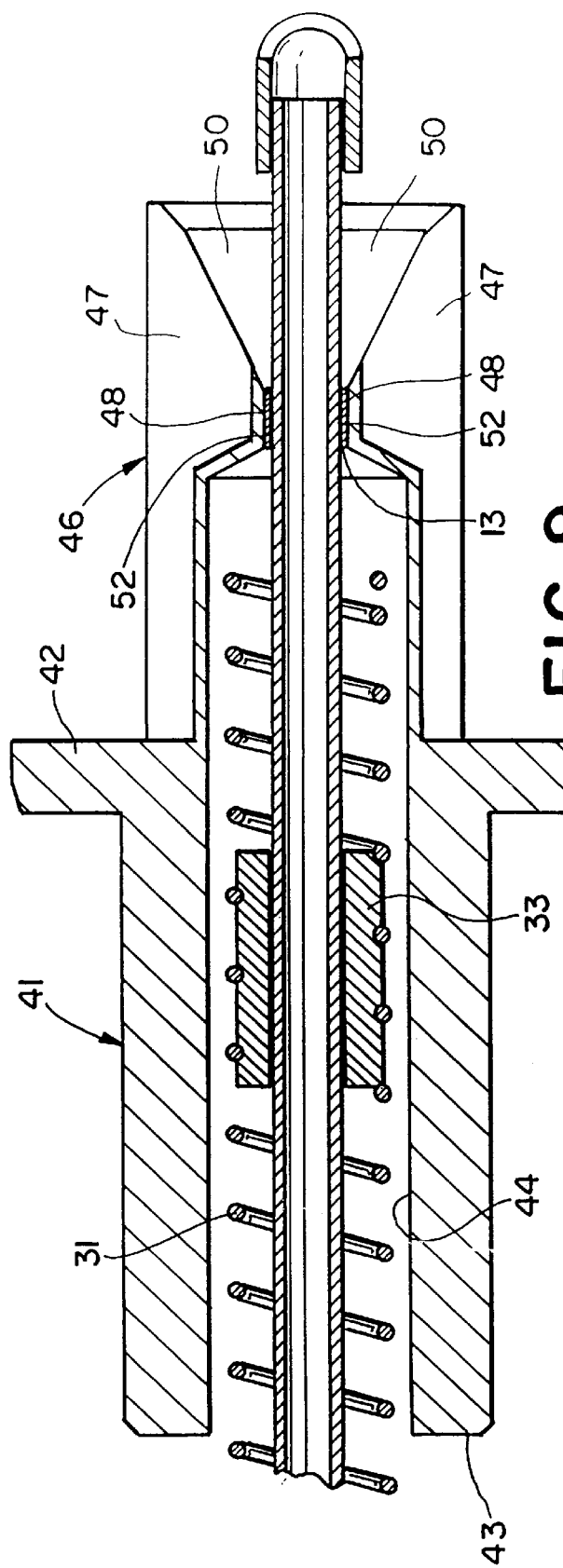
FIG. 9 is an enlarged sectional view of the needle retainer with the associated needle and biasing spring of the fluid collection device of FIG. 1.

The engagement between the needle 15 and the needle retainer 41 is best seen in the enlarged view in FIG. 9. The latching structure or mechanism is preferably divided into a plurality of latching projections or fingers 47, which are formed at the rear end of the needle retainer 41. When the needle retainer is positioned in the needle carrier, the fingers 47 extend axially rearward into the interior of the barrel 3 of the needle carrier 2. The fingers 47 are formed to have radially inwardly directed protrusions having interior surfaces 48, forming a constricted portion 13 in bore 44 of the needle retainer. The surfaces 48 are substantially parallel to the axial surface of the needle 15. The surfaces 48 are configured to conform to the outer surface of the needle 15 to thereby maintain the needle 15 in axial alignment within the needle retainer 41. The surfaces 48 of the fingers 47 preferably form a continuous surface within the interior of the needle retainer 41 to enhance engagement with the needle 15. The continuous axial surface between the fingers 47 also provides a seal with the needle 15, so that fluid is kept out of the axial bore 44 in the needle retainer 41 during use in collecting fluid.

The surfaces 48 of the fingers 47 are secured or bonded to the outer surface of the needle 15 using an adhesive 52, such as one of the adhesives or epoxies listed in Table 1 below. The preferred adhesive 52 for a particular application will depend on such variables as the strength of the spring 31, the surface area of the constricted portion 13 of the bore 44, and the material of which the fingers 47 and the needle are manufactured.

TABLE 1

| Adhesive Type | Supplier Designation | Supplier |
| --- | --- | --- |
| Epoxy | EP30 | MasterBond |
| Epoxy | EP21LV | MasterBond |
| Epoxy | 301 RTC | Epoxy Technology |
| Epoxy | 353 RTC | Epoxy Technology |
| Epoxy | E32 | Permabond |
| Epoxy | C-7/A-34 | Armstrong |
| Epoxy | 3501 B/A Grey | Scotch-Weld |
| Epoxy | 3501 B/A Clear | Scotch-Weld |
| Epoxy | Henkel Versamid 125 catalyst/Shell Epon 828 resin | Henkel/Shell |
| Epoxy | Eccobond 1962-31 | W. R. Grace |
| Epoxy | Eccobond 927-10E | W. R. Grace |
| Epoxy | FDA-2 | Tracon |
| Epoxy | Eccobond LA 2843-23 | W. R. Grace |
| Cyanoacrylate | 4011 | Loctite |
| Cyanoacrylate | 4013 | Loctite |
| Cyanoacrylate | 4161 | Loctite |
| UV cured adhesive | 3001 | Loctite |
| UV cured adhesive | 3011 | Loctite |
| UV cured adhesive | UV 9006 | W. R. Grace |
| UV cured adhesive | UV 9007 | W. R. Grace |
| UV cured adhesive | UV 9008 | W. R. Grace |

As can be seen most clearly in FIG. 8, the needle retainer preferable comprises four fingers 47, but more or less fingers 47 may be employed depending on such factors as the size of the device and the nature of the biasing member (i.e., spring 31), for effecting optimum operation in holding the needle and facilitating needle retraction.

The exterior of needle retainer 41 is provided with longitudinal grooves or score lines 49 between the fingers 47 to facilitate separation of the fingers and breakage of the fingers 47 when the retraction of the needle is actuated.

In the initial configuration of the needle carrier shown in FIG. 1, the needle retainer 41 is positioned in the forward portion of the barrel. The spring 31 surrounds the needle 15 and is compressed between the rear of the sealing member 35 at the forward end 4 of the barrel 3 and the location at which the spring 31 is bonded to the needle 15 by adhesive 33. Hence, the needle 15 is biased toward the rear end 5 of the barrel 3 of the needle carrier 2 and is held by the needle retainer fingers 47 against the bias of the spring.

Referring again to FIG. 9, the fingers 47 are preferably flexible to permit outward movement to break the bond between the needle 15 and the retainer surfaces 48 in order to release the fingers 47 from the needle 15. Additionally, the fingers could be fractured when moved outwardly to release the needle. The fingers 47 are formed to have canted or wedge-shaped rearwardly facing surfaces 50 to facilitate engagement and spreading of the fingers 47, as described more fully herein below. As shown in FIG. 10, when the fingers 47 are deformed or flexed radially outwardly to release the fingers 47 from the needle 15, the expansive force of the spring 31 immediately thrusts the needle 15 toward the rear end 5 of the barrel 3 of the needle carrier 2. Thus, the sharp end of the needle 15 is drawn into the barrel 3 to prevent accidental touching of the needle after use.

Referring again to FIG. 2, an actuating member generally designated 53 is slidably positioned in the rear end 5 of the barrel 3 of the needle carrier 2. The actuating member 53 is manufactured from a material which is chemically compatible with the fluid being collected. For example, the actuating member 53 may be made from polystyrene, which is suitable for use with blood collection devices. Alternatively, chemical compatibility may be provided by a conformal coating or layer of a chemically inert material, such as polytetrafluoroethylene, upon the surfaces of the actuating member 53 that come into contact with the fluid being collected.

The actuating member 53 is generally cylindrical and is adapted to be received within the rear end of the barrel 3. The actuating member 53 has a flange 54 formed thereon for engagement with the interior of the barrel 3 to position and guide the actuating member during movement. A detent 9 is formed on the inner surface of the barrel 3 so that the flange 54 can be forced by the detent 9 during assembly, and thereafter prevented from being withdrawn from the barrel 3.

The actuating member 53 includes structural features for effecting release of the needle 15 from the needle retainer 41. The forward end of the actuating member 53 comprises a tapered head 66 formed thereon, which provides a frustro-conical forward surface. The forward surface of the head 66 provides an annular shoulder that is complementarily contoured or tapered to mate with the outwardly flared rearward surfaces 50 of the fingers 47 of the needle retainer 41. To release the bond between the surfaces 48 of the fingers 47 and the needle 15, the actuating member 53 is urged forward within the barrel 3 to spread the fingers outward by cooperative engagement between the head 66 and the rear surfaces 50 of the fingers, as shown in FIG. 10.

In the as-shipped configuration shown in FIG. 2, the actuating member 53 is initially located at its initial or rearward position in the barrel 3, such that the flange 54 abuts with the detent 9 at the rear of the barrel 3. The head 66 of the actuating member 53, in addition to providing a release mechanism for the needle 15, is sized to provide a fluid seal between the interior of the barrel 3 and the periphery of the head 66. During shipment or storage of the needle carrier, the material of which the actuating member 53 and the head 66 are formed may creep or deform to compromise the integrity of the fluid seal provided by the head 66. In order to ensure a fluid tight seal prior to use of the device, the barrel 3 includes a reduced-diameter portion 10 located along the interior surface of the barrel 3 in the forward direction relative to the first position of the head 66. Immediately prior to use of the needle carrier, the actuating member 53 is advanced within the body to a second or intermediate, position as shown in FIG. 1. In the second position of the actuating member 53, the head 66 is positioned within the reduced diameter portion 10 of the barrel 3. The constrictive force exerted on the head 66 by the interior of the barrel 3 insures the integrity of the fluid seal provided therebetween. Advancement of the actuating member 53 to the second position is automatically effected when the holder adapter 82 is connected to the needle carrier, as described hereinbelow.

Referring again to FIG. 2, the actuating member 53 has a hollow interior defining a chamber 56 having an open forward end 58 and a partially-closed or reduced diameter open rear end 57. The chamber 56 is sized to allow the needle 15 along with the attached spring 31 to be received into the chamber 56. The rear end 57 of the chamber 56 has an axial bore 60 formed therein which has a smaller diameter than the chamber 56. Accordingly, a rear wall 67 is formed where the axial bore 60 adjoins the chamber 56. When the actuating member 53 is actuated for retraction of the needle 15, the spring 31 propels the needle rearwardly 15. The needle 15 and spring 31 are thereby propelled toward the rear of the chamber 56, and the rear wall 67 acts as a stop for the spring 31 and the needle 15. The rear end of the actuating member 53 is shown in greater detail in FIG. 13.

The axial bore 60 holds the rear needle 68 in a fixed, rearwardly projecting position. A forward portion 71 of the rear needle 68 is held in the reduced diameter, axial bore 60. The clearance provided between the rear needle 68 and the axial bore 60 is selected to substantially prevent fluid passage between the rear needle 68 and the actuating member 53. A rear portion 73 of the rear needle 68 extends beyond the rear end of the actuating member 53. To ensure that the rear needle 68 does not become dislodged from the actuating member 53, the rear needle 68 may be secured in place by an adhesive 78. A rearwardly projecting, axial extension 81 is formed on the rear end 59 of the actuating member 53 to further support and align for the rear needle 68. The extension 81 comprises a tubular section which is concentric with the axial bore 60 and which has an inner diameter of substantially the same dimension as the axial bore 60.

An elastomeric boot 74 is positioned over the rear portion 73 of the rear needle 68. During insertion of the device into the patient's vein, the boot 74 prevents fluid from prematurely flowing out from the needle carrier 2, and provides a visual indicator, when it receives fluid, that the needle 15 is properly inserted within the vein of the patient. When the needle 15 is properly inserted into the patient, fluid flows through the needle 15 and fills a "flashback" chamber defined by the interior of the barrel 3 of the needle carrier 2, the chamber 56 of the actuating member 53, the lumen 72 of the rear needle 68, and the interior of the boot 74. To facilitate such operation, gas is vented from the flashback chamber by hairline vent or grooves 76 formed between the boot 74 and the actuating member 53. In an alternative embodiment shown in FIG. 14, such venting may be provided by a vent hole 77 formed in the boot 74. Whether venting is provided by grooves or holes, such apertures are desirably sized to allow the surface tension and viscosity of the collected fluid, e.g., blood, to prevent such fluid from leaking from the device through the apertures.

Referring again to FIG. 1, the holder adapter 82 comprises a housing 83 which is configured to be removably engaged to the barrel 3 of the needle carrier 2. The forward end 84 of the housing 83 comprises an axial bore 88 having internal threads 111 for engagement with corresponding external threads 112 found on the rear end of the barrel 3 of the needle carrier 2.

A concentric tubular forward portion 113 extends rearwardly to form the forward end of the tube adapter 82. The tubular portion has an inwardly-directed lip 89 formed thereon. The lip 89 is positioned to abut with a radial flange 61 on the actuating member 53 to drive the actuating member into the second or intermediate position within the barrel 3 of the needle carrier 2, when the holder adapter 82 is fixed or connected to the needle carrier. As the tube adapter 82 is screwed onto the needle carrier 2, the forward surface of the lip 89 pushes on the rear surface of the radial flange 61, thereby forcing the actuating member 53 to move forward within the barrel 3 of the needle carrier 2 until the head 66 of the actuating member 53 is positioned in the reduced diameter portion 10 of the barrel 3.

The holder adapter 82 includes a gate or safety actuator mechanism generally designated 87 to prevent accidental or premature retraction of the needle 15. The gate mechanism preferably comprises a slide member 91 extends across the interior of the housing 83 of holder adapter 82. An eccentric bore 92 is formed through the slide member 91. The slide member 91 is transversely slidable within the housing 83 from a locked position to an unlocked position. The eccentric bore 92 is formed in the slide member 91 to facilitate the slide member acting as a step for flange 63 of the actuating member. Hence, the bore 92 is ordinarily displaced from the longitudinal axis of the actuating member 53 so that the rear surface of slide member 91 abuts with a flange 63 of the actuating member 53 in a locked position to prevent forward motion of the actuating member 53, avoiding inadvertent premature retraction of the needle 15.

The slide member 91 further includes a biasing portion 94 for biasing the slide member 91 to the locked position. The biasing portion 94 is sufficiently flexible to yield when a transverse force is applied to displace the slide member 91 towards an unlocked position. In the unlocked position, the bore 92 is aligned with the flange 63, so that the actuating member 53 can be further moved toward the front of the barrel. The biasing portion 94 is sufficiently resilient to return to its original shape when the transverse force is released. The biasing portion 94 is provided by a portion of the slide member which is formed to provide a biasing member.

To facilitate connection of the holder adapter 82 to the needle carrier 2, the rear end 59 of the actuating member 53 may have a conical camming surface 64 for aligning the slide member 91 with the longitudinal axis of the actuating member during installation of the holder adapter 82 onto the needle carrier 2. Hence, as the holder adapter 82 is mated to the rear of the needle carrier, the camming surface 64 urges the rim of the eccentric bore 92 into alignment with the actuating member 53. Then, when the tube adapter reaches the position shown in FIG. 2, the biasing portion 94 urges the slide member 91 into overlapping abutment with flange 63.

A slide button or actuator 97 is provided on the exterior of the housing 83 to facilitate activation of the slide member 91 prior to retracting the needle 15. In the configuration shown in FIG. 3, the slide button 97 can be pushed rearwardly by the user to cause the slide member 91 to be moved transversely from the locked position to the unlocked position. The button 97 has a slanted or beveled inner surface 98 formed thereon to abut with a slanted outer surface 95 of the slide member 91 in order to cam against the outer surface 95 when the button is pushed. The outer surface of the button 97 may include ridges or serrations 96 to provide traction with the user's finger. In an alternative embodiment (not shown), the button can be designed to be depressed in order to move the slide member from the locked position to the unlocked position.

External projections, providing finger grips 100, are formed along the exterior of the housing 83 of the holder adapter 82 to allow the user to more easily maneuver and manipulate the device. In a preferred embodiment, the finger grips 100 are positioned so that the user can grip the device between two fingers while exerting forward pressure against the rear of the collection tube 105 to maneuver a collection tube into position and cause retraction of the needle, as explained below.

The rear end of the holder adapter 82 is sized to receive a collection tube 105 for receiving the fluid to be collected. The collection tube 105 comprises a generally cylindrical body 106 having a closed rear end 107 and an open forward end 108. The forward end 108 of the collection tube 105 is sealed by a puncturable plug member 109. In this arrangement, an interior chamber 110 is defined within the collection tube 105. The plug 109 seals the forward end 108 of the collection tube 105 so that a vacuum or reduced pressure can be maintained within the chamber 110. The collection tube 105 can be removably inserted into the holder adapter 82 by inserting the forward end 108 of the collection tube 105 into the housing 83 of the holder adapter 82. As the collection tube 105 is inserted, the rear needle 68 punctures the plug 109.

As previously mentioned, when the needle 15 is released from the needle retainer 41, the needle is thrust rearwardly to be received in the chamber 56 of the actuating member 53. Because the needle 15 may contain a volume of residual fluid therein, it is desirable to prevent such fluid from being ejected from the forward end of the needle as the needle is accelerated rearwardly by the spring during needle retraction. Accordingly, there is provided means for preventing such ejection of fluid from the needle of blood collection device of the present invention. One such means is a check valve 19, which may be mounted to the rear end of the needle 15 for preventing fluid from being expelled through the forward end of the needle 15 as the needle 15 is being retracted.

As shown in detail in FIG. 5, the check valve 19 comprises an elastomeric cap 20 which is formed to fit over the rear end of the needle 15. The cap 20 has a cylindrical portion 22 with an axial bore 23 for securing the cap 20 onto the needle 15. The cap 20 has a slit 21 formed in the rear end of the cap 20, so that the slit opens as fluid moves rearwardly through the needle but fluid is prevented from passing through the slit 21 in a forward direction. Hence, as the needle is accelerated toward the rear of the needle carrier, the slit closes to seal the rear of the needle 15 to prevent fluid or gas from entering the rear of the needle to displace any fluid that would otherwise be ejected from the forward end of the needle, and providing a partial vacuum within the rear of the needle to retain residual fluid therein.

An alternative embodiment of a check valve for the end of the needle 15 is shown in FIG. 6 and comprises a ball valve 119. The ball valve 119 has a cap 120 which fits over the rear end of the needle. The cap 120 has a cylindrical portion 122 with an axial bore 123 for securing the cap 120 to the needle. A rear portion 126 of the cap 120 forms an enclosure 124 having a bore 125. The bore 125 of the enclosure 124 is in axial alignment and fluid communication with the bore 123 of the cylindrical portion 122 of the cap 120. A ball 128 is captured within the enclosure 124 of the cap 120. The ball 128 is sized to loosely fit within the enclosure 124. When the ball 128 is in a forward position, the ball 128 seals the bore 125 of the cap 120 and prevents gas or fluid from entering the cylindrical portion 122 of the cap 120 and, hence, the rear end of the needle. When the ball 128 is in a rearward position, fluid is free to flow through the needle, around the ball 128, and out through opening 121 in the rear portion 126 of the cap 120. During fluid collection, the ball is displaced toward the rear of the enclosure 124 by the flow of fluid through the needle. When the needle is accelerated rearwardly, the ball is urged against the forward end of the enclosure 124 to seal the rear end of the needle.

In still another embodiment of means to prevent ejection of fluid from the needle during retraction, there is shown in FIG. 7 an arrangement comprising a hole 229 formed in the side of the needle 215 and a plug 230 positioned in the rear end 218 of the needle. The needle 15 of FIG. 1 is indicated by the number 215 in FIG. 7. In this embodiment, when the needle 215 is propelled rearwardly during retraction of the needle 215, gas or fluid in the chamber, into which the needle is moving, is forced to flow over the closed rear end of the needle 215, as indicated by lines 216. The hole 229 is positioned sufficiently toward the rear of the needle such that it is located adjacent a region 217 of reduced air pressure created by the stream lines 216 of fluid or gas around the closed rear end of the needle. For needles having sizes ranging from 25 gauge to 20 gauge, holes of about 0.020 to about 0.080 inches in diameter located at about 0.030 to about 0.10 inches from the rear end of the needle are within a range effective to substantially prevent fluid from being ejected from the forward end of the needle as it is accelerated rearwardly into retraction. In a preferred embodiment of a 21 gauge needle, a hole of about 0.05 inches in diameter centered at about 0.07 inches from the rear end of the needle has been shown to be effective. In other embodiments, such parameters as the length and mass of the needle, and the force constant of the spring, will affect the selection of appropriate dimensional parameters for determining the arrangement for preventing forward fluid ejection.

Figure 4:
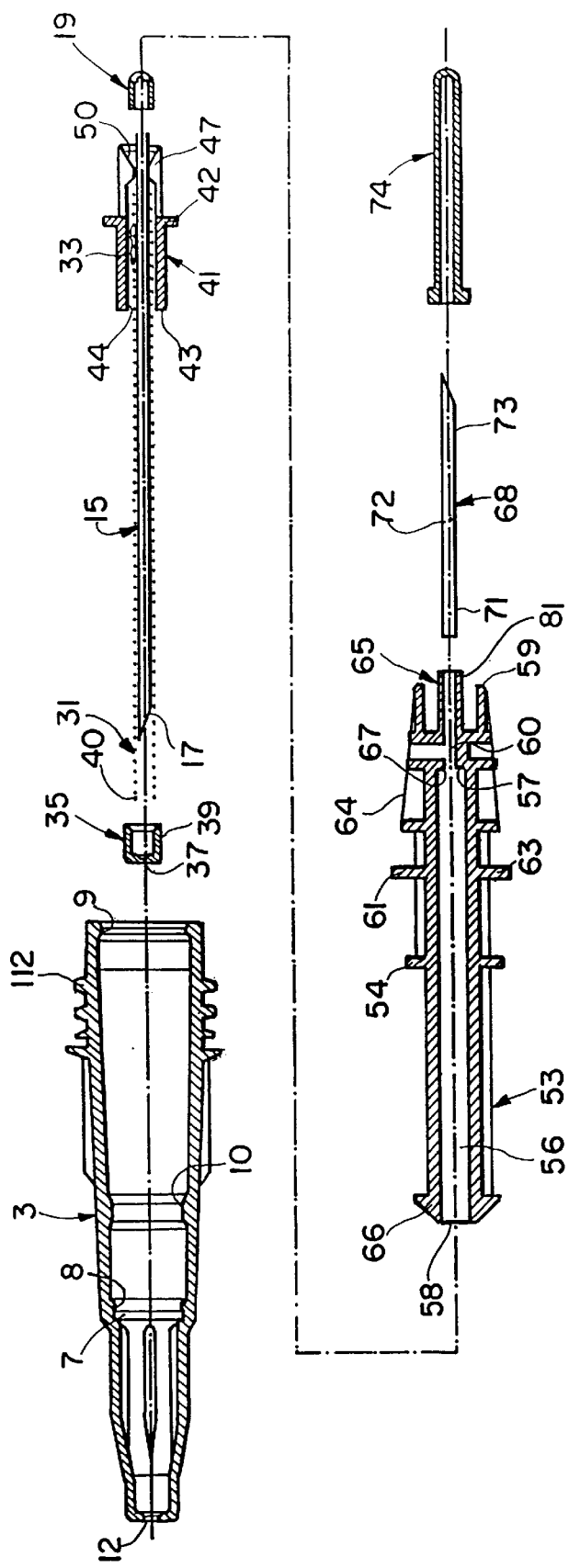
FIG. 4 is an exploded sectional view of the needle retainer assembly of FIG. 1.

The needle carrier 2 can be assembled as shown with reference to the exploded view of FIG. 4. The spring 31 is bonded to the needle 15 with adhesive 33. The needle 15 is then axially positioned within the needle retainer 41. The surfaces 48 of the needle retainer 41 are then secured to the needle 15. Valve 19 is positioned onto the rear end of the needle 15. The sealing member 35 is positioned in the forward portion of the barrel 3 of the needle carrier 2. Alternatively, the sealing member 35 can be positioned onto the forward end 40 of the spring 31. The needle retainer 41, needle 15, and spring 31 are then inserted into the rear end 5 of the barrel 3 of the needle carrier 2 until the needle retainer 41 seats within groove 7 on the interior of the barrel 3 of the needle carrier 2.

The forward portion 71 of the rear needle 68 is then secured in the axial bore 60 of the actuating member 53. The boot 74 is positioned over the rear needle 68 and secured to the rear end of the actuating member 53. The forward end 55 of the actuating member 53 is then inserted into the rear end of the needle carrier 2. The actuating member 53 is advanced to the initial or first position within the barrel 3, so that the first radial flange 54 of the actuating member 53 passes over the second detent 9 along the inner surface of the barrel 3 of the needle carrier 2. If the device is not to be used at this time, front and rear caps, 79 and 80, are then positioned over the needle 15 and the rear needle 68, as shown in FIG. 2.

Prior to use of the device, the front and/or rear caps, 79 and 80, are removed from the needle carrier 2. The holder adapter 82 is mounted on the needle carrier 2 by engaging the internal threads 111 on the holder adapter 82 with the external threads 112 of the needle carrier 2 in a screw-type motion to assume the configuration shown in FIG. 1. The screwing motion causes the lip 89 on the tubular portion 113 of the tube adapter 82 to advance the actuating member 53 to the second position, such that the forward end of the actuating member 53 is in close proximity to the rear portion 45 of the needle retainer 41. In the second position, the radial flange 63 of the actuating member 53 abuts against the slide member 91 of the safety actuator or gate mechanism 87.

The needle 15 can then be inserted into a patient (i.e., into a blood vessel of the patient for blood sampling). The user then verifies that the needle 15 is properly inserted in the patient's blood vessel by looking for the appearance of fluid in the flashback chamber area in the needle carrier 2. When the needle 15 has been properly inserted into the patient, the collection tube 105 is inserted by the user into the rear end of the tube adapter 82. As the collection tube 105 is advanced therein, the rear needle 68 pierces the boot 74 and the plug 109, and the boot 74 is compressed by the plug 109 down the shaft of the rear needle. When the rear end of the rear needle 68 enters the chamber 110 of the collection tube 105, fluid is drawn into the chamber 110 of the collection tube 105 by the vacuum or reduced pressure within the collection tube 105.

When the collection tube 105 is filled, or a desired amount of fluid has been collected, the collection tube 105 can be withdrawn from the holder adapter 82. Subsequent collection tubes can be filled in substantially the same manner. When the last desired collection tube has been filled, the needle 15 is withdrawn from the patient's blood vessel while maintaining the collection tube in the holder adapter 82.

The needle 15 can now be retracted by the user. To initiate retraction, the device can be gripped between two of the user's fingers while the rear end 107 of the collection tube 105 is positioned against the palm of the user's hand. For example, if the barrel is held between the thumb and the middle finger, the rear of the collection tube 105 may be placed against the palm, while the index finger is extended along the barrel to actuate the button 97 of the safety gate mechanism. The button 97 is then moved rearwardly, thereby laterally displacing the slide member 91 within the barrel to bring the eccentric bore 92 of the slide member 91 into axial alignment with the flange 63 of the actuating member 53. While maintaining the slide member 91 in the unlocked position, the collection tube 105 is further advanced in a forward direction relative to the barrel by applying pressure to the rear end 107 of the collection tube 105 with the palm of the user's hand. Movement of the collection tube 105 in the forward direction urges the forward end of the actuating member 53 against the fingers 47 on the needle retainer 41. The fingers 47 are thereupon spread radially outwardly by the force of the forward end of the actuating member 53. When the fingers 47 are spread radially outwardly, the surfaces 48 of the fingers 47 are disengaged from the needle 15, that is the bond between the fingers and needle is broken. Accordingly, the needle 15 is then propelled rearwardly, by expansion of the biasing spring 31, into the chamber 56 of the actuating member 53. The needle 15 in its retracted position in the device is shown in FIG. 3. The collection tube 105 can then be removed and the needle carrier 2 and holder adapter 82 can safely be discarded. Alternatively, the holder adapter may be removed from the needle carrier for subsequent re-use.

It should be appreciated that the structure disclosed herein for retaining the needle, as well as the structure for releasing the fingers of the needle retainer from the needle by breaking a bond therebetween, are applicable to a wide variety of medical devices other than the fluid collection device described herein. For example, the needle holding and retraction arrangement can be used in syringes, pre-filled syringe ampoules, and catheter insertion devices to effect selective holding and retraction of the needles of such devices. The retraction of the needle enhances the safety of personnel engaged in the use or disposal of such devices, and further prevents reuse of used devices. Moreover, the confidence of the user is enhanced by the provision of a means for preventing premature retraction of the needle. In needle-bearing devices constructed in accordance with the foregoing principles, a compound action requiring simultaneous operative forces to be applied to distinct portions of the device is required in order to effect retraction of the needle.

The terms and expressions which have been employed are used as terms of description and not of limitation. There is no intention in the use of such terms and expressions of excluding any equivalents of the features shown and described or portions thereof. It will be recognized by those skilled in the art that changes or modifications may be made to the above-described embodiments without departing from the broad inventive concepts of the invention. It should therefore be understood that this invention is not limited to That which is claimed is:

1. A needle-bearing medical device having a retractable needle with a sharpened tip for penetrating the skin of a patient for diagnostic or therapeutic purposes, the device comprising:
   a barrel;
   a needle retainer positioned in the barrel and holding the needle axially to project forward from the barrel in an initial configuration;
   an actuating member positioned in the barrel and operable by the user to effect automatic retraction of the needle into the barrel after use; and
   fluid retention means associated with the needle for substantially preventing ejection of residual fluid from the needle during retraction of the needle.

2. The device of claim 1 wherein the fluid retention means comprises means for producing a partial vacuum within the rear of the needle during retraction.

3. The device of claim 1 wherein the fluid retention means comprises a one way valve connected with the rear of the needle.

4. The device of claim 3 wherein the one way valve comprises a ball valve.

5. The device of claim 3 wherein the one way valve comprises a resilient member having a resealable opening formed therein and configured to allow fluid flow in one direction and substantially resist fluid flow in an opposite direction.

6. The device of claim 5 wherein the resealable opening in the resilient member comprises a slit formed therein to provide the resealable opening.

7. The device of claim 1 wherein the fluid retention means comprises a closure in the rear end of the needle, the needle having an aperture formed through a side thereof at a location toward the rear of the needle to be positioned adjacent a zone of reduced pressure along the needle during retraction of a needle.

8. A hand-held medical device, comprising a barrel;
   a needle projecting forward from the barrel and having a sharpened tip for penetrating the skin of a patient for transmitting fluid for diagnostic or therapeutic purposes;
   an automatic needle retraction mechanism positioned in the barrel and actuable by a user to effect retraction of the needle into the barrel after use; and
   fluid retention means associated with the needle for substantially preventing ejection of residual fluid from the needle during retraction of the needle.

9. The device of claim 8 wherein the needle retraction mechanism comprises:
   a spring connected with the needle and compressed within the barrel to exert a rearward bias upon the needle;
   a needle retainer for holding the needle in an initial projecting configuration against the bias exerted by the spring;
   a first actuating member positioned in the housing and operable by the user to release the needle retainer from holding the needle.

10. The device of claim 9 comprising an actuator member configured to prevent operation of the actuating member such that a compound operation of both the actuating member and actuator member is required to effect retraction of the needle.

11. The device of claim 10 comprising a second needle positioned to extend rearwardly from the barrel, and a housing connected with the barrel and configured to receive a sampling vial therein for penetration by the second needle.

12. The device of claim 11 wherein the second needle extends rearwardly from the actuating member, such that actuation of the actuating member is operable by urging against the rear of the vial.

13. The device of claim 10 wherein the actuating member and actuator member are configured to be operated by the user along distinct directional axes to effect retraction.

14. The device of claim 13 wherein the actuating member comprises a tubular member positioned in the barrel and axially advanceable therein to release the needle retainer; and wherein the actuator member comprises an interference gate for selectively preventing advancement of the tubular member.

15. The device of claim 14 wherein the tubular member includes an abutment surface thereon, and wherein the interference gate is configured to engage the abutment surface; said actuator member being operable by the user to disengage the gate from the abutment surface.

16. The device of claim 15 wherein the actuator member includes a resilient member for biasing the gate into engagement with the abutment surface.

17. The device of claim 16 comprising a second needle positioned to extend rearwardly from the actuating member, and a housing connected with the barrel and configured to receive a sampling vial therein for penetration by the second needle, such that actuation of the actuating member is operable by urging against the rear of the vial.

18. The device of claim 17 wherein the actuator member is connected with an actuating surface positioned along a side of the housing, such that a compound operation is required and actuating force applied to the actuating surface of the actuator member and to the rear of the vial in contact with the actuating member for effecting retraction of the needle.

19. A hand-held medical device, comprising:
   a barrel;
   a needle projecting forward from the barrel and having a sharpened tip for penetrating the skin of a patient;
   a spring connected with the needle and compressed within the barrel to exert a rearward bias upon the needle;
   a needle retainer for holding the needle in an initial projecting configuration from the barrel against the bias exerted by the spring;
   an actuating member positioned in the housing and operable by the user to release the needle retainer from holding the needle; and
   an actuator member configured to prevent operation of the actuating member, such that a compound operation of both the actuator member and the actuating members is required to effect retraction of the needle.

20. The device of claim 19 comprising a second needle positioned to extend rearwardly from the barrel, and a housing connected with the barrel and configured to receive a sampling vial therein for penetration by the second needle.

21. The device of claim 20 wherein the second needle extends rearwardly from the actuating member, such that actuation of the actuating member is operable by urging the rear of the vial into the housing.

22. The device of claim 19 wherein the actuator member and actuating member are configured to be operated by the user along distinct directional axes to effect retraction.

23. The device of claim 22 wherein the actuating member comprises a tubular member positioned in the barrel and axially advanceable therein to release the needle retainer; and wherein the actuator member comprises an interference gate for selectively preventing advancement of the tubular member.

24. The device of claim 23 wherein the tubular member includes an abutment surface thereon, and wherein the interference gate is configured to engage the abutment surface; said actuator member being operable by the user to disengage the gate from the abutment surface.

25. The device of claim 24 wherein the actuator member includes a resilient member for biasing the gate into engagement with the abutment surface.

26. The device of claim 25 comprising a second needle positioned to extend rearwardly from the actuating member, and a housing connected with the barrel and configured to receive a sampling vial therein for penetration by the second needle, such that actuation of the actuating member is operable by urging against the rear of the vial.

27. The device of claim 26 wherein the actuator member is connected with an actuating surface positioned along a side of the housing, such that a compound operation is required and actuating force to be applied to the actuating surface of the actuator member and to the rear of the vial in contact with the actuating member for effecting retraction of the needle.

28. An automatic needle retraction mechanism for a needle-bearing medical device having a barrel, the retraction mechanism comprising:

a spring connected to the needle and compressed within the barrel for exerting a bias upon the needle for withdrawing the needle into the barrel;

a needle retainer positioned in the barrel and bonded to the needle for restraining the needle against the bias exerted by the spring; and an actuating member slidably positioned in the barrel and configured for disengaging the needle retainer from the needle upon advancement of the actuating member against the needle retainer.

29. The retraction mechanism of claim 28 wherein the needle retainer comprises a plurality of separable fingers configured to provide a continuous interior surface bonded to the needle.

30. The retraction mechanism of claim 29 wherein the bonding surface is adhesively bound to the exterior of the needle, and wherein the actuating member is configured to break the adhesive bond between the needle retainer and the needle.

31. In a medical device comprising a barrel and an actuating member slidably positioned in the barrel, a fluid seal comprising:

an integral head portion formed on the actuating member having an integral annular peripheral surface in contact with the interior of the barrel; the barrel having a constricted portion formed therein and the actuating member being positioned in the barrel initially at a first position prior to use and slidable to a second position in the barrel to have the head located within the constricted portion of the barrel, whereby a fluid seal is provided during use.

* * * * *